United States Patent [19]

Seidel

[11] 4,075,297
[45] Feb. 21, 1978

[54] ANESTHETIC VAPORIZER

[75] Inventor: Peter Seidel, Lubeck, Germany

[73] Assignee: Dragerwerk Aktiengesellschaft, Germany

[21] Appl. No.: 659,233

[22] Filed: Feb. 19, 1976

[30] Foreign Application Priority Data

Feb. 20, 1975   Germany .............................. 2507262

[51] Int. Cl.² ............................................ A61M 17/00
[52] U.S. Cl. .................................... 261/104; 128/188; 261/DIG. 65
[58] Field of Search .................. 261/99, DIG. 65, 104, 261/107, 110; 128/185–192, 211

[56] References Cited

U.S. PATENT DOCUMENTS

| 2,442,004 | 5/1948 | Hayward-Butt | 128/188 |
| 3,651,805 | 3/1972 | Breiling | 128/188 |
| 3,713,440 | 1/1973 | Nicholes | 128/188 |

FOREIGN PATENT DOCUMENTS

| 54,378 | 3/1943 | Netherlands | 128/187 |

*Primary Examiner*—Tim R. Miles
*Assistant Examiner*—Gregory N. Clements
*Attorney, Agent, or Firm*—McGlew and Tuttle

[57] ABSTRACT

An anesthetic vaporizer comprises a housing having a liquid reservoir and a vaporizing chamber over the reservoir. A gas inlet into the housing provides for flow through a vaporizing passage and into the vaporizing chamber for subsequent flow outwardly above the chamber, through an outlet vaporizing passage, to an outlet for discharge to the place of use. The vaporizing passage includes a spirally wound wick tube disposed between an interior wall of the housing and an interior barrel of cylindrical shape which retains the tube in position. In addition a bypass passage connects the inlet to the outlet passage and a control is provided for regulating the flow through at least one of the passages so as to regulate the amount of the circulated gas which is enriched with vaporized anesthetic.

5 Claims, 1 Drawing Figure

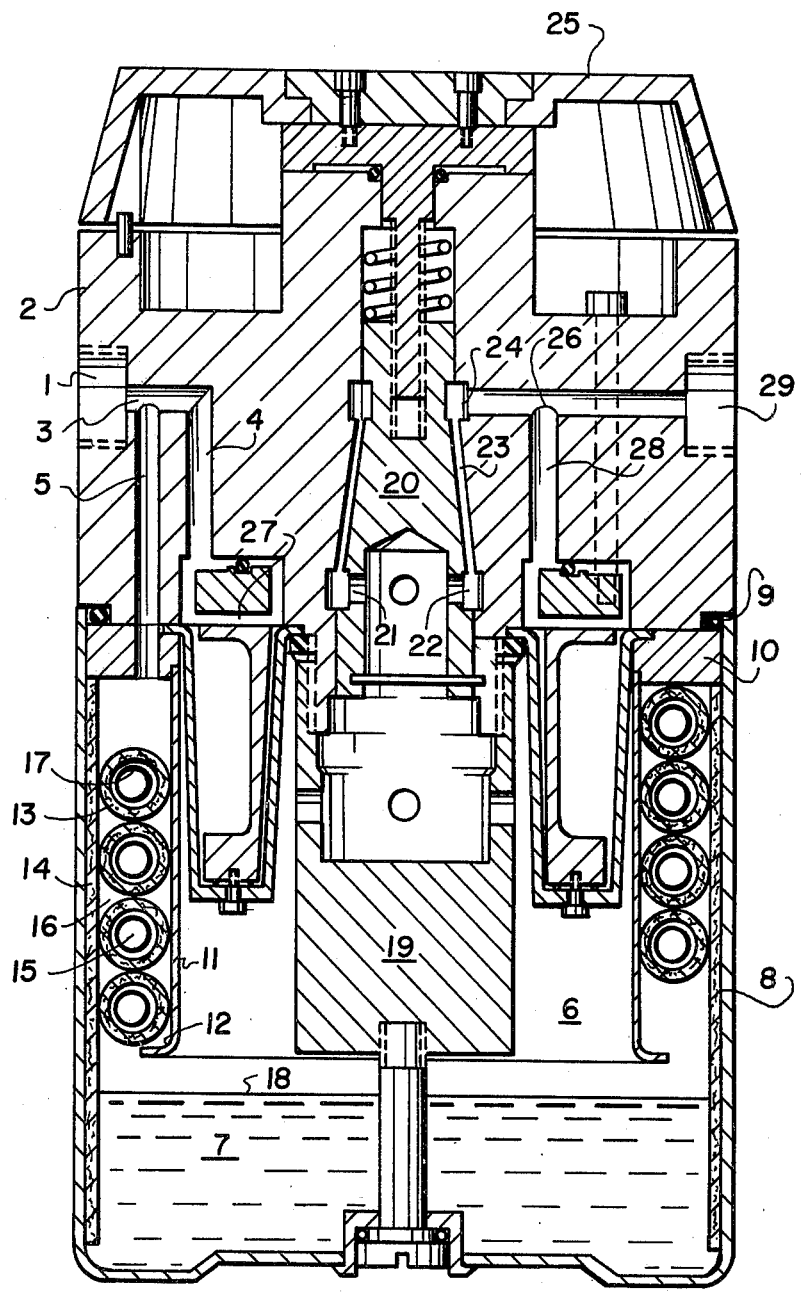

ANESTHETIC VAPORIZER

BACKGROUND OF THE INVENTION

1. Field of the Invention

This invention relates in general to the construction of vaporizers and in particular to a new and useful anesthetic vaporizer which includes a bypass line connecting the gas inlet with the gas outlet and a guide for the flow of the portion of the gas to be vaporized through the vaporizing chamber and for subsequently combining it with the bypass gas.

2. Description of the Prior Art

In anesthetic vaporizers, a gas current passing through the vaporizing chamber over a reservoir of the anesthetic is enriched with the anesthetic to a desired concentration. In the known bypass anesthetic vaporizers, the desired dosing is obtained by dividing a total current into a bypass current, comprising a part of the total gas current in an unchanged gas composition, and into the vaporizing chamber current. The vaporizing chamber current comprises the balance of the total gas flow and this is enriched in the vaporizing chamber with the anesthetic in order to saturate it. This is generally achieved by passing vaporizing chamber current over a wick which dips into the liquid and which is saturated by capillary action with the liquid anesthetic. The gas is passed over the wick for as long as necessary to saturate the gas in accordance with its vapor pressure at the respective temperature. In order to insure saturation of the vaporizer chamber current with the anesthetic under all circumstances, that is also at maximum flow, a relatively large evaporation surface and thus a large vaporizer chamber volume are required.

But a large vaporizer chamber volume cannot counteract the necessary constancy of the anesthetic concentration at a pressure variation which occurs during respiration or use of the gas in breathing. This is because the vaporizer chamber current can get into the bypass line in an expansion of the respiratory gas from the vaporizer chamber backwardly. In this way inadmissibly high concentrations can be formed at the outlet of the anesthetic vaporizer.

A known bypass anesthetic vaporizer has two wicks designed as cylinders and they differ slightly in their diameter so that an annular interval, corresponding to the diameter difference, is formed between them, and which are assembled at the same level. The larger wick cylinder is arranged on the inside of the cylindrical chamber wall forming the vaporizer chamber. The smaller wick cylinder bears on the outside diameter of a cavity reducer arranged in the cavity of the vaporizer chamber. The bottom ends of the two wick cylinders protrude into a liquid anesthetic. The vaporizer chamber current enters into the vaporizer chamber from the top, flows over the surface of the anesthetic and is enriched slightly with the anesthetic and issues again through an annular interval between the two wick cylinders, which are wetted with the anesthetic by capillary action, and flows upwardly from the vaporizing chamber and combines with the bypass current.

The generatrix of the wick cylinders is very small compared to the space required for their combination. The flow conditions and thus the evaporation of the anesthetic can be insured optimally in the narrow and not exactly defined annular interval between the wick cylinders. In order to insure the necessary saturation of the vaporizer chamber current under all circumstances, the wick cylinders, and thus also the space which determines the dimensions of the anesthetic vaporizers, are made very large. The large cavity formed by this design of the wicks must be reduced by a cavity reducer and this only increases the weight of the vaporizer in order to prevent the dreaded return of the vaporizer chamber current at pressure variations during the respiration.

Another known anesthetic vaporizer according to the bypass system has similar wick cylinders but they are separated by a circumferential gas carrying spiral. This insures a uniform spacing distance. Besides, the spiral forces the anesthetic to flow over a certain path past the wick surfaces saturated with the anesthetic. The return of the vaporizer chamber current at pressure variations caused by the respiration is to be prevented by a pressure compensation spiral. This is arranged above the wick cylinders. The vaporizer chamber current flows in the order pressure compensation spiral, the spiral interval and the anesthetic surface, and combines again with the bypass current. Even an anesthetic vaporizer of this type is still very large. This, in addition to the space requirement, impairs its handiness.

SUMMARY OF THE INVENTION

The invention improves the efficiency of a vaporizer and provides a simple construction which is very handy to operate and one in which the size of the vaporizing chamber is reduced. This is achieved if the pressure compensation is improved at the same time. In accordance with the invention, this is accomplished by forming a guide with a wick system which consists of a spirally wound tube, which bears on the inside of a cylindrical wick surface, dipping into the anesthetic and which is held by a cylindrical barrel.

The advantages of the construction are that a large evaporation surface of the anesthetic is provided which meets the requirement for a high evaporation efficiency and also permits the use of a handy small vaporizer chamber. The vaporizer chamber current entering the vaporizer chamber flows with one part through the wick tube and the other part through an interval between the spirals of the tube and the wick barrel up to the surface of the anesthetic. The anesthetic surface is thus, in the first partial current, the entire surface of the wick tube, and, in the second partial current, the inner surface of the wick barrel and also the outer surface of the wick tube. The pressure compensation is improved by the spiral arrangement of the wick tube. The return of the vaporizer chamber current is prevented, at pressure variations, by a braking effect in the two partial currents.

In accordance with the invention, the wick tube contains in its interior a supporting insert which can be a spiral spring. With this simple arrangement the wick tube is always held with its cross section open. This insures a maximum evaporation surface on the inside and the outside. The insert insures, in addition, closure during the assembly between the wall of the vaporizer chamber and the wick barrel along with the wick tube and the cylinder barrel arranged on the inside thereof. This construction results in a particularly simple assembly which reduces the cost of inspections and also its manufacture.

The simple assembly and also the secured arrangement of the wick tube at the proper point is enhanced by a flange provided at the bottom end of the cylinder barrel and which extends under the bottom edge of the wick tube to support it in its position therein.

Accordingly it is an object of the invention to provide an improved anesthetic vaporizer which comprises a housing having a vaporizing chamber located over a reservoir of anesthetic, with a gas inlet into the housing which is connectable to the vaporizing chamber through a first passage which extends through the interior of, and externally around, a sprirally wound wick tube held between an inner cylindrical barrel and a wick barrel on the interior surface of the lateral wall of the housing and from which the entering gas passes over the liquid to be vaporized and issues upwardly through a discharge passage to a discharge opening, and which also includes a bypass passage which connects the inlet directly to the discharge passage for combining the by-pass gas with the portion of the gas which has already been vaporized.

A further object of the invention is to provide a vaporizer in which a wick tube is mounted within a housing between an internal cylindrical barrel and an the interior surface of a lateral wall, and is advantageously provided with an interior spring to hold the walls of the wick tube open, wherein the barrel includes a lower outwardly directed end supporting the lower end of the tube without any other support.

A further object of the invention is to provide a vaporizer which is simple in design, rugged in construction and economical to manufacture.

For an understanding of the principles of the invention, reference is made to the following description of a typical embodiment thereof as illustrated in the accompanying drawings.

BRIEF DESCRIPTION OF THE DRAWINGS

The only FIGURE of the drawing is an axial sectional view of a vaporizer constructed in accordance with the invention.

GENERAL DESCRIPTION OF THE PREFERRED EMBODIMENT

Referring to the drawings in particular, the invention embodied therein comprises a vaporizer which includes a housing 2 having a gas inlet 1 which splits into two separate flow streams at a separation point 3. The partial vaporizing chamber current passes through a vaporizing chamber line or vaporization passage 5 and a partial bypass current passes through a bypass line 4. The interior of the housing carries a reservoir for liquid anesthetic 7 and defines a vaporizing chamber 6 above the reservoir. The vaporizing chamber 6 is closed to the outside by a pot 8 which is joined gastight with the housing 2 by gasket 9. The gasket 9 is held in position by a ring 10. The ring 10 carries on its inside circumference the cylinder or wick tube support barrel 11.

In accordance with the invention, the cylinder or wick tube support barrel 11 is formed with an outturned bottom end, bend, or flange 12 forming a support for the wick tube 13 by extending at least partially beneath the lower end of the wick tube 13. The portion of the gas steam which flows downwardly through the passage 5 splits, and a part of it flows through the interior of the tube 13 after entering the open top end of the spiral tube, with another part flowing, around the exterior of the tube 13, through the spiral space defined between the tube 13, the wick barrel 14 and the cylindrical tube support barrel 11. It will be noted that the successive convolutions of the wick tube 13 rest upon each other, with the bottom convolution being supported on the bend or flange 12, and it will be further noted that the lower end of the wick barrel 14 advantageously dips into the liquid anesthetic. The space 16 between the wick barrel 14 and the wick tube support barrel 11, and further defined by the convolutions of the spiral wick tube 13, provides an additional vaporizing space for the flow of the partial stream. The wick tube 13 is supported on its inside by a spiral spring 17 which extends completely therethrough. The part of the stream which flows on the outside past the wick barrel 14 also flows along the wick barrel length. Both the wick barrel 14 and the wick tube 13 are saturated with anesthetic by capillary action. The contact between the wick tube 13 and the wick barrel 14 is achieved and insured by the cylinder barrel 11 provided with the bend 12. Additional fastening is not necessary.

The cylinder barrel or wick tube barrel 11 insures by its length that the vaporizer chamber current can still flow above the surface 18 of the liquid anesthetic into the vaporizer chamber 6. The vaporizer chamber current saturated with anesthetic issues from the vaporizer chamber 6 and flows along the guide piece 19 for the gas into the dosing cone 20 from which it is conducted through bores or a discharge passage 21 into the ring canal 22. From the ring canal 22 it passes through a cone gap 23 and into a ring canal 24. The cone gap 23 is formed by the housing 2 and the dosing cone 20 which is adjustable upwardly and downwardly by means of a hand wheel 25 to vary the size of the cone gap 23. The vaporizer chamber current joins with the bypass current downstream of the ring canal 24 at the junction 26. The bypass current flows through the bypass line 4 and the dosing clearance 27 and also through one or several bores 28 to the junction 26. There the vaporizer chamber current and the bypass current mix and leave the anesthetic vaporizer jointly through the gas outlet opening 29.

Other features of this construction are disclosed in copending patent application Ser. No. 657,219 filed Feb. 11, 1976, and entitled "Vaporizer for Anasthetics".

What is claimed is:

1. An anesthetic vaporizer comprising a housing, including a lateral wall, defining an interior liquid reservoir and a vaporizing chamber above said reservoir, a gas inlet into said housing, a cylindrical wick tube support barrel supported in said vaporizing chamber and spaced inwardly from the inner surface of said lateral wall of said housing, a wick barrel on the interior surface of said lateral wall, with its lower end extending into the liquid in said liquid reservoir, a spirally wound wick tube, open at both ends, disposed between said tube support barrel and said wick barrel and supported, at its lower end, solely by said wick tube support barrel, with its adjacent convolutions in contact with each other, means defining a vaporizing gas passage in said housing communicating at one end with said inlet and at its opposite end with the interior of said tube through the open upper end thereof and with the space defined between convolutions of said spirally wound wick tube, said wick barrel and said wick tube support barrel, said vaporizing gas passage providing for flow of gas from said inlet through the interior of said tube and over the exterior thereof to said reservoir, a vaporizer outlet from said housing, means defining an outlet passage connecting said vaporizer chamber to said vaporizer outlet, means defining a by-pass passage extending from said gas inlet to said vaporizer outlet, and a supporting insert in said wick tube extending completely therethrough between the open ends thereof, said supporting insert maintaining said wick tube completely open for the flow of gas therethrough.

2. An anesthetic vaporizer according to claim 1, including means for varying the capacity of said outlet passage.

3. An anesthetic vaporizer according to claim 2, including a central conical member in said outlet passage spaced from a portion of said housing and defining a gap between said housing and said conical member, and a handle connected to said conical member to displace it in said housing for varying the size of said gap between said conical member and said housing and the size of said outlet passage.

4. An anesthetic vaporizer according to claim 1, wherein said insert comprises a spiral spring.

5. An anesthetic vaporizer according to claim 1, wherein said wick tube support barrel includes an outturned lower end extending under said wick tube and supporting the lower end thereof.

* * * * *